US011440858B2

(12) United States Patent
Watson et al.

(10) Patent No.: US 11,440,858 B2
(45) Date of Patent: Sep. 13, 2022

(54) METHOD OF IMPROVING OLEFIN ISOMERIZATION

(71) Applicant: Lyondell Chemical Technology, L.P., Houston, TX (US)

(72) Inventors: Rick B. Watson, Houston, TX (US); David W. Leyshon, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 17/519,884

(22) Filed: Nov. 5, 2021

(65) Prior Publication Data

US 2022/0135500 A1   May 5, 2022

Related U.S. Application Data

(60) Provisional application No. 63/110,185, filed on Nov. 5, 2020.

(51) Int. Cl.
  *C07C 5/27*   (2006.01)
  *B01J 29/65*  (2006.01)
  *B01J 29/88*  (2006.01)

(52) U.S. Cl.
  CPC .......... *C07C 5/2708* (2013.01); *B01J 29/88* (2013.01); *C07B 2200/09* (2013.01); *C07C 2529/88* (2013.01)

(58) Field of Classification Search
  CPC ... C07C 5/2713; C07C 5/2716; C07C 5/2718; C07C 5/2721; C07C 5/2724;
  (Continued)

(56) References Cited

U.S. PATENT DOCUMENTS 3,933,974 A   1/1976  Winquist
4,000,248 A  12/1976  Martin
         (Continued)

FOREIGN PATENT DOCUMENTS

EP       523838 A2   1/1993

OTHER PUBLICATIONS

The International Search Report and The Written Opinion of The International Searching Authority for PCT/JS2021/058200 dated Feb. 10, 2022.

(Continued)

*Primary Examiner* — In Suk C Bullock
*Assistant Examiner* — Jason Y Chong

(57) ABSTRACT

A skeletal isomerization process for isomerizing olefins is described. The process includes the steps of feeding an olefin-containing feed to a reactor at a space velocity of 1-100 $hr^{-1}$ for a first period of time at a first temperature, followed by discontinuing, or stopping, the olefin-containing feed for a second period of time while maintaining the reactor at a second temperature, before resuming the flow of the olefin-containing feed for a third period of time. The methods of this disclosure increase the yield of the skeletal isomers product while reducing the production of C5+ heavy olefins. Additionally, the methods of this disclosure can be applied to feeds containing iso-olefins (for the production of linear olefins) or linear olefins (for the production of iso-olefins).

15 Claims, 8 Drawing Sheets

(58) Field of Classification Search
CPC .............. C07C 5/2727; C07C 2529/65; C07C 2529/88; B01J 29/65; B01J 29/88; B01J 2229/123; B01J 2229/42; C07B 2200/09
See application file for complete search history.

(56) References Cited

U.S. PATENT DOCUMENTS

| | | |
|---|---|---|
| 4,942,027 A | 7/1990 | Evans |
| 5,648,585 A | 7/1997 | Murray et al. |
| 5,817,907 A * | 10/1998 | Benazzi ............... B01J 29/7046 585/671 |
| 6,111,160 A | 8/2000 | Powers et al. |
| 6,323,384 B1 | 11/2001 | Powers et al. |
| 9,827,560 B2 | 11/2017 | Petushkov et al. |

OTHER PUBLICATIONS

Collett et al., Things Go Better with Coke: The Beneficial Role of Carbonaceous Deposits in Heterogeneous Catalysis, The Royal Society Chemistry 2016, Catalysis Science & Technology, 2016, 6, pp. 363-378.
Guisnet et al., Skeletal Isomerization of n-Butenes, Journal of Catalysis, 1990, 158, pp. 551-560.
Wen-Qing Xu et al., Coke Formation and Its Effects on Shape Selective Adsorptive and Catalytic Properties of Ferrierites, J. Phys. Chem., 1995, 99, pp. 758-765.
Cañizares et al., Isomerization of n-Butene over Ferrierite Zeolite Modified by Silicon Tetrachloride Treatment, Applied Catalysis A: General, 2000, 190, pp. 93-105.

* cited by examiner

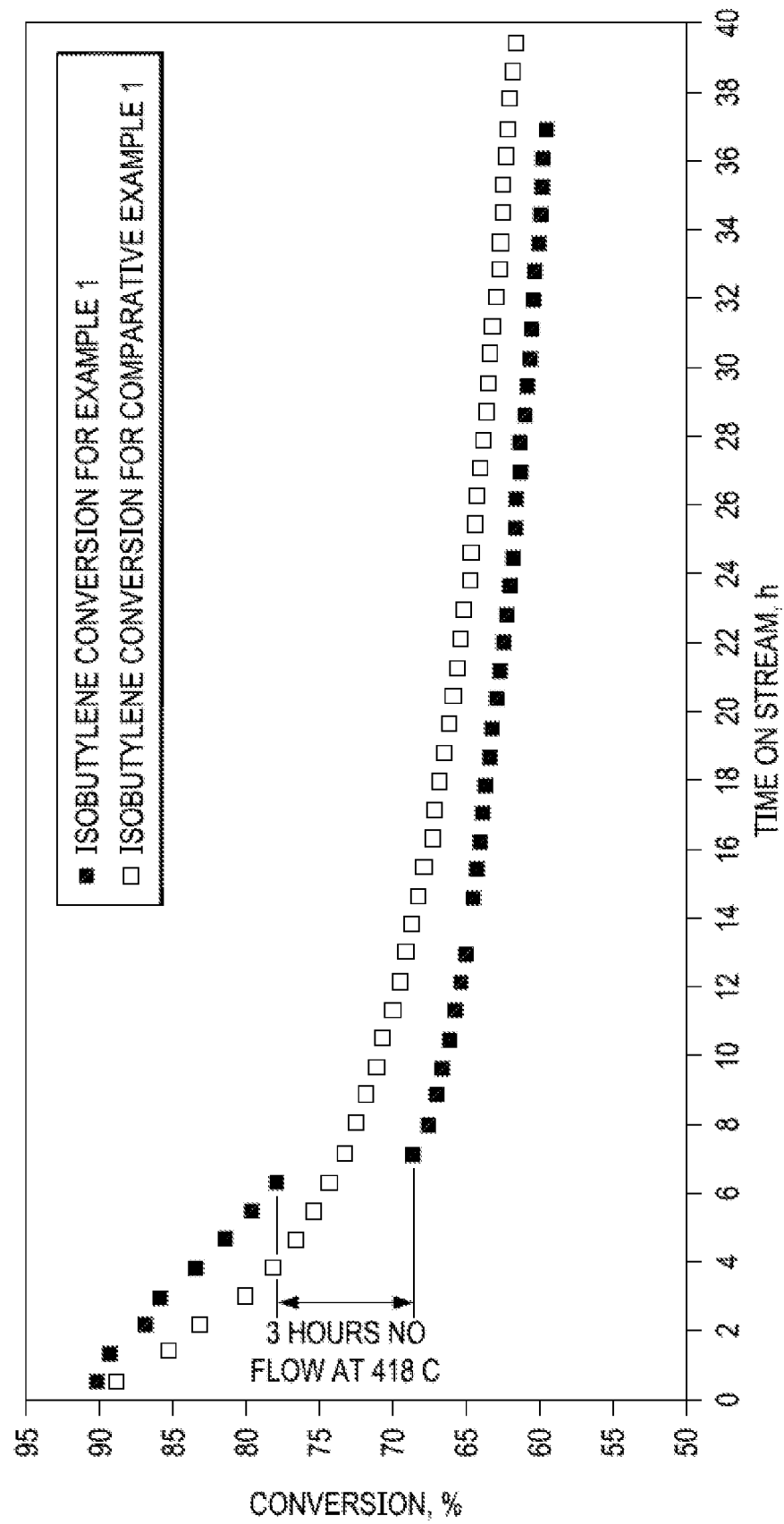

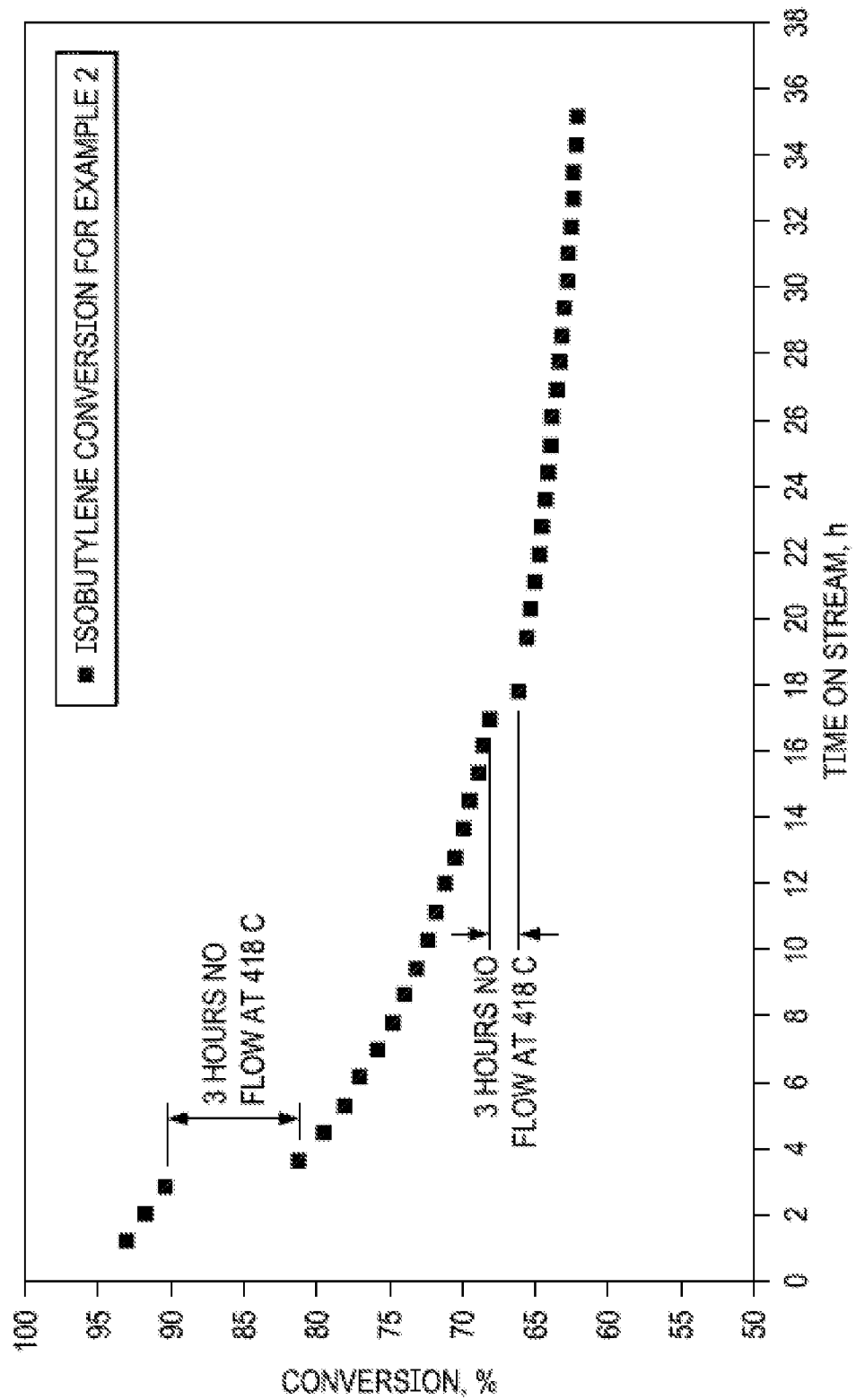

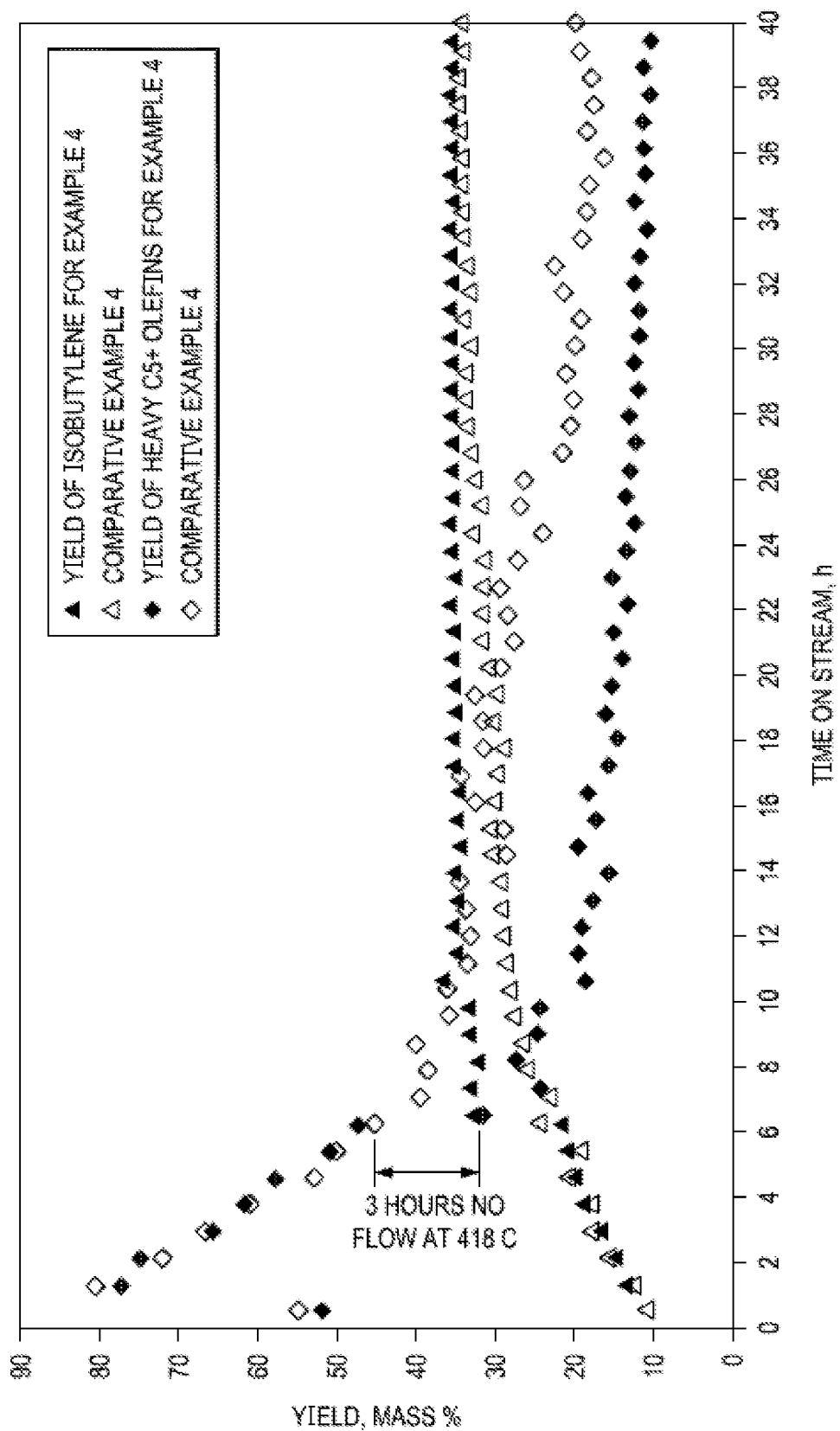

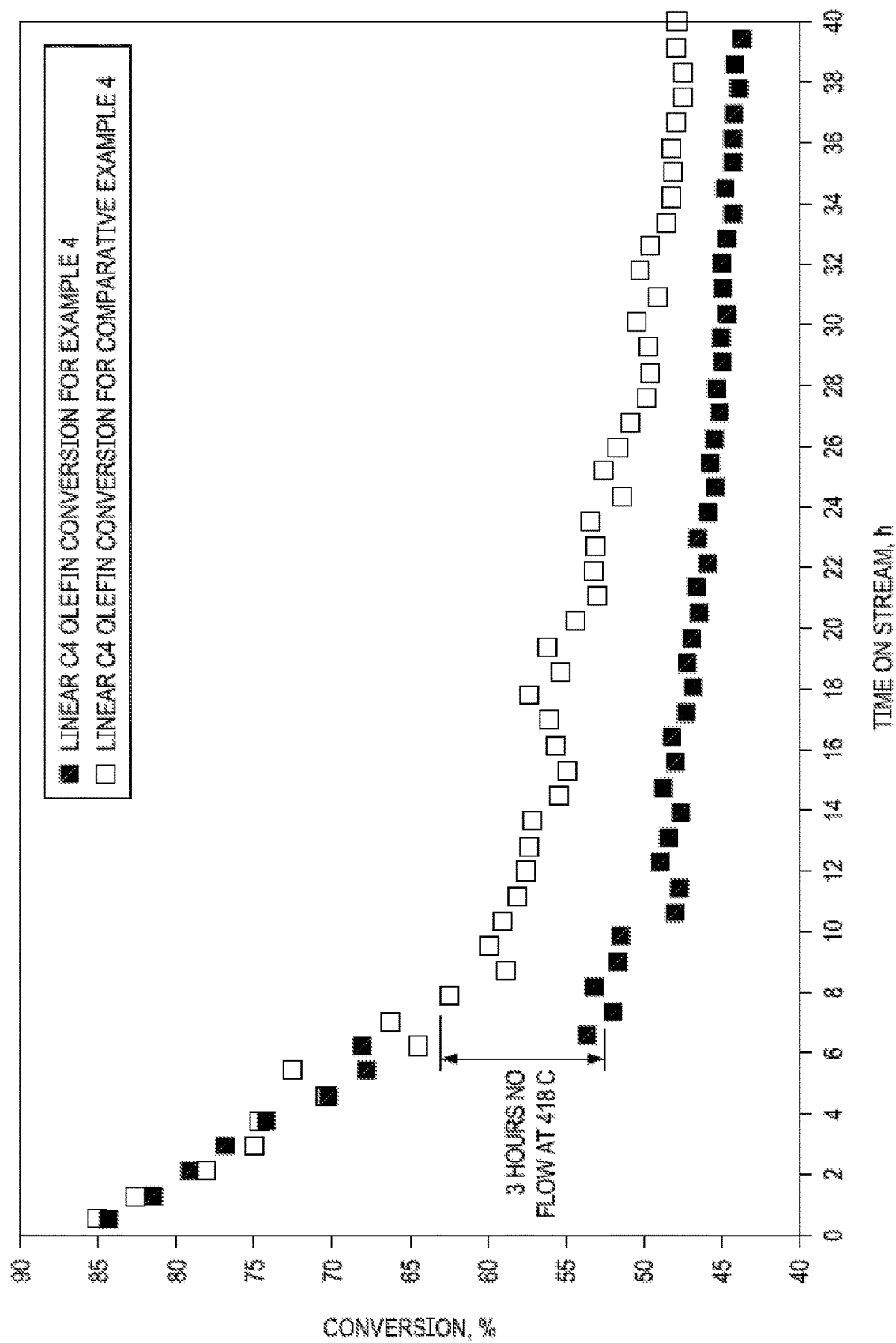

METHOD OF IMPROVING OLEFIN ISOMERIZATION

PRIOR RELATED APPLICATIONS

This application claims the benefit of priority to U.S. Provisional Patent Application No. 63/110,185, filed on Nov. 5, 2020, which is incorporated herein by reference in its entirely.

FEDERALLY SPONSORED RESEARCH STATEMENT

Not applicable.

FIELD OF THE DISCLOSURE

The disclosure generally relates to skeletal isomerization processes, and more specifically to a method of improving the performance of an olefin skeletal isomerization process.

BACKGROUND OF THE DISCLOSURE

In many instances, it is desirable to convert a methyl branched alkene such as isobutylene, to a linear alkene, such as 1-butene, by mechanisms such as skeletal isomerization. It is known, by the demand for Patent EP 0523 838 (Lyondell), that it is possible to use a process of skeletal isomerization of branched olefin, such as isobutylene, using a catalyst of zeolite type having a structure and a dimension of channels adapted especially to produce linear olefins and to reduce coking.

Zeolite materials, both natural and synthetic, are known to have catalytic properties for many hydrocarbon processes. Zeolites are ordered porous crystalline aluminosilicates having a definite structure with cavities interconnected by channels. The cavities and channels throughout the crystalline material can be of such a size to allow selective reaction of hydrocarbons. Such a hydrocarbon reactions by the crystalline aluminosilicates essentially depends on discrimination between molecular dimensions. Consequently, these materials in many instances are known in the art as "molecular sieves" and are used, in addition to catalytic properties, for certain selective adsorptive processes. Zeolite molecular sieves are discussed in great detail in D. W. Breck, Zeolite Molecular Sieves, Robert E. Krieger Publishing Company, Malabar, Fla. (1984).

However, during the isomerization process, a portion of the olefin molecules aggregate at or in the channels of the zeolite catalyst, on adjacent active sites, resulting in dimerization or oligomerization that lead to byproducts of longer chains and heavier molecular weights than the desired product. Consequently, the yield and conversion rate of the desired product is reduced, particularly in the beginning hours of the time-on-stream. During this period of unselective transformation, coke is deposited on the catalyst surface and the yield of beneficial products increases with time while that of undesired products decreases. The coke deposited in this initial period of time is deemed beneficial in that it diminished the unselective transformations. This positive benefit of initial coking has been cited in the isomerization of n-butene over ferrierite catalysts. Several examples of the benefit of pre or preferential coking in several hydrocarbon conversion processes can be found in the literature.

There is the need for an economical process that can effectively produce the beneficial coke deposition increasing the yield and conversion rate to the isomerization product while reducing the production of byproducts.

SUMMARY OF THE DISCLOSURE

The present disclosure is directed to novel methods for structurally isomerizing hydrocarbon streams containing one or more olefins. In particular, a skeletal isomerization process that includes one or more periods of time where the flow of the olefin feed into the reactor has been halted is disclosed. Without being bound to any particular theory, it is suspected that "beneficial" coking of the unselective sites on the catalyst occurs during this stagnation phase. Specifically, while the olefin feed is interrupted, dimers or oligomers of the olefin form in the channels of the catalyst and may form coke in situ. This coking of the unselective sites reduces the subsequent production of heavy byproducts, herein referred to as "C5+ heavies", due to fewer active sites now being available on the catalyst. Further, the yield of the isomerization product increases by at least 5%.

Some aspects of the presently disclosed method comprises the steps of: (a) providing a feed comprising one or more olefin, for a first period of time, at a weight hourly space velocity (WHSV) in the range of from 1 to 100 $hr^{-1}$ to a reactor containing a catalyst, wherein the reactor is maintained at a first temperature during the first period of time; (b) halting the feed comprising the one or more olefin to the reactor for a second period of time and stagnating the reactor flow, wherein the reactor is maintained at a second temperature during the second period of time; and (c) resume feeding the feed comprising the one or more olefin to the reactor wherein at least a portion of the one or more olefin in the feed is structurally isomerized to a skeletal isomer. The method can also comprise repeating steps (b) and (c), in order, one or more times.

Alternatively, the presently disclosed method comprises the steps of: (a) feeding, for a first period of time, a feed comprising one or more olefin to a reactor having a catalyst wherein the feeding of the feed has a weight hourly space velocity (WHSV) from 1 to 100 $hr^{-1}$, wherein the reactor is maintained at a temperature in the range of from 400° C. to 420° C., and wherein the first period of time is from about 1 to 5 hours; (b) stopping, for a second period of time, the feeding of the feed, wherein the second period of time is about 1 to 5 hours, and wherein the reactor is maintained at a temperature in the range of from 400° C. to 450° C.; and (c) resuming, for a third period of time, the feeding of the feed to the reactor, wherein the reactor is maintained at a temperature in the range of from 400° C. to 420° C. The temperature in the first and third period of time may be the same or may be different. The method can also comprise additional periods of flow stoppage and flow resumption, in order, one or more times using the same conditions as the second and third period of time, or it can have different conditions that are within the ranges described for (b) and (c).

In some aspects of the present methods, the olefin feed comprises branched, iso-olefins, wherein the skeletal isomerization process converts the branched, iso-olefins to unbranched, linear olefins, which are also referred to as normal olefins. In other aspects of the present methods, the olefin feed comprises linear olefins which are then converted to branched iso-olefins during the novel skeletal isomerization process. The olefins in either feed can have 2 to 10 carbons. The feed may also include other hydrocarbons such as alkanes, other olefins, aromatics, hydrogen, and inert gases.

The present methods and systems include any of the following embodiments in any combination(s) of one or more thereof:

A: A skeletal isomerization method comprising the steps of: (a) providing a feed comprising at least one olefin, for a first period of time, at a weight hourly space velocity (WHSV) in the range of from 1 to 100 $hr^{-1}$ to a reactor containing a catalyst, wherein the reactor is maintained at a first temperature during the first period of time; (b) halting the feed comprising the at least one olefin to the reactor for a second period of time, wherein the reactor is maintained at a second temperature during the second period of time; and (c) resuming the feed comprising the at least one olefin to the reactor wherein at least a portion of the at least one olefin in the feed is isomerized to at least on skeletal isomer.

B: A process for the production of a linear olefin comprising the steps of: (a) providing a feed comprising an iso-olefin, for a first period of time, at a weight hourly space velocity (WHSV) in the range of from 1 to 100 $hr^{-1}$ to a reactor containing a catalyst, wherein the reactor is maintained at a first temperature during the first period of time; (b) halting the feed comprising the iso-olefin to the reactor for a second period of time, wherein the reactor is maintained at a second temperature during the second period of time; and (c) resuming the feed comprising the iso-olefin to the reactor wherein at least a portion of the iso-olefin in the feed is isomerized to the linear olefin.

C: A process for structurally isomerizing 2-methylprop-1-ene ("isobutylene") to a linear C4 olefin skeletal isomer, comprising the steps of: (a) feeding a feed comprising isobutylene to a reactor having a catalyst for a first period of time, wherein the feeding of isobutylene has a weight hour space velocity (WHSV) from 1 to 100 $hr^{-1}$, and wherein the reactor is maintained at a temperature in the range of from 400° C. to 420° C. for 1 to 5 hours; (b) stopping the feeding of isobutylene for 1 to 5 hours, wherein the reactor is maintained at a temperature in the range of from 400° C. to 450° C.; and (c) resuming the feeding of isobutylene, wherein the reactor is maintained at the first temperature, wherein the isobutylene is isomerized to a linear C4 olefin.

D: A process for the production of an iso-olefin comprising the steps of: (a) providing a feed comprising at least one linear olefin, for a first period of time, at a weight hourly space velocity (WHSV) in the range of from 1 to 100 $hr^{-1}$ to a reactor containing a catalyst, wherein the reactor is maintained at a first temperature during the first period of time; (b) halting the feed comprising the at least one linear olefin to the reactor for a second period of time, wherein the reactor is maintained at a second temperature during the second period of time; and (c) resuming the feed comprising the at least one linear olefin to the reactor wherein at least a portion of the at least one linear olefin in the feed is isomerized to the iso-olefin.

E: A process for structurally isomerizing linear C4 olefin to isobutylene (its skeletal isomer), comprising the steps of: (a) feeding a feed comprising linear C4 olefin to a reactor having a catalyst for a first period of time, wherein the feeding of linear C4 olefin has a weight hour space velocity (WHSV) from 1 to 100 $hr^{-1}$, and wherein the reactor is maintained at a temperature in the range of from 400° C. to 420° C. for 1 to 5 hours; (b) stopping the feeding of linear C4 olefin for 1 to 5 hours, wherein the reactor is maintained at a temperature in the range of from 400° C. to 450° C.; and (c) resuming the feeding of the linear C4 olefin, wherein the reactor is maintained at the first temperature and wherein at least a portion of the linear C4 olefin in the feed is isomerized to the isobutylene.

Each of embodiments A, B, C, D, and E may have one or more of the following additional elements:

Element 1: wherein during the second period of time coking of the catalyst increases. Element 2: additionally, comprising recovering linear olefins from the reactor. Element 3: wherein the feed comprises at least 40 wt. % isobutylene. Element 4: wherein the feed comprises at least 55 wt. % isobutylene. Element 5: wherein the feed comprises at least 70 wt. % isobutylene. Element 6: wherein the feed comprises at least 85 wt. % isobutylene. Element 7: wherein the feed comprises at least 95 wt. % isobutylene. Element 8: wherein the feed comprises at least 99 wt. % isobutylene. Element 9: wherein the iso-olefin is isobutylene. Element 10: wherein the linear C4 olefin is one or more of 1-butene, cis-2-butene, or trans-2-butene. Element 11: wherein the WHSV of the feed during the first period of time ranges from 1 to 80 $hr^{-1}$. Element 12: wherein the WHSV of the feed during the first period of time ranges from 10 to 50 $hr^{-1}$. Element 13: wherein the WHSV of the feed during the first period of time ranges from 35 to 65 $hr^{-1}$. Element 14: wherein the WHSV of the feed during the first period of time ranges from 1 to 20 $hr^{-1}$. Element 15: wherein the WHSV of the feed during the third period of time is the same as the WHSV of the feed during the first period of time. Element 16: wherein the WHSV of the feed during the third period of time ranges from 1 to 100 $hr^{-1}$. Element 17 wherein the WHSV of the feed during the third period of time ranges from 1 to 80 $hr^{-1}$. Element 18: wherein the WHSV of the feed during the third period of time ranges from 10 to 50 $hr^{-1}$. Element 19: wherein the WHSV of the feed during the third period of time ranges from 35 to 65 $hr^{-1}$. Element 20: wherein the WHSV of the feed during the third period of time ranges from 1 to 20 $hr^{-1}$. Element 21: wherein the first temperature is in the range of from 350° C. to 450° C. Element 22: wherein the first temperature is in the range of from 370° C. to 410° C. Element 23: wherein the first temperature is in the range of from 380° C. to 425° C. Element 24: wherein the first temperature is in the range of from 400° C. to 420° C. Element 25: wherein the second temperature is in the range of from 350° C. to 450° C. Element 26: wherein the second temperature is selected from the same range of temperatures as the first temperature. Element 27: wherein the second temperature is the same as the first temperature. Element 28: wherein the second temperature is higher than the first temperature. Element 29: wherein the second temperature is in the range of from 400° C. to 430° C. Element 30: wherein the second temperature is in the range of from 420° C. to 450° C. Element 31: wherein upon resuming the feed comprising the iso-olefins to the reactor, the reactor is maintained at a third temperature. Element 32: wherein the third temperature is in the range of from 350° C. to 450° C. Element 33: wherein the third temperature is selected from the same range of temperatures as the first temperature. Element 34: wherein the third temperature is the same as the first temperature. Element 35: wherein the third temperature is higher than the first temperature. Element 36: wherein the third temperature is in the range of from 370° C. to 410° C. Element 37: wherein the third temperature is in the range of from 380° C. to 425° C. Element 38: wherein the third temperature is in the range of from 400° C. to 420° C. Element 39: wherein the first period of time is from 1 to 10 hours. Element 40: wherein the first period of time is from 2 to 7 hours. Element 41: wherein the first period of time is from 2 to 5 hours. Element 42: wherein the first period of time is from 4 to 6 hours. Element 43: wherein the second period of time is selected from the same range of times as the first period of time. Element 44: wherein the second period of time is the same as the first period of time. Element 45: wherein the second period of time is longer than the first period of time. Element 46: wherein the second period of time is shorter than the first period of time. Element 47: wherein the second period of time is from 2 to 7 hours. Element 48: wherein the second period of time is from 2 to 5 hours. Element 49: wherein the second period of time is from 4 to 6 hours. Element 50: wherein the reactor is maintained at a pressure less than 1034 kPa (150 psig) during the first period of time. Element 51: wherein the reactor is maintained at a pressure less than 345 kPa (50 psig) during the first period of time. Element 52: wherein the reactor is maintained at a pressure less than 1034 kPa (150 psig) after resuming the feed comprising the iso-olefin. Element 53: wherein the reactor is maintained at a pressure less than 345 kPa (50 psig) after resuming the feed comprising the iso-olefin. Element 54: wherein the feed is introduced into the reactor at a temperature of about 380° C. to about 425° C. and a pressure from about zero to about 345 kPa (50 psig). Element 55: wherein the catalyst is a zeolite catalyst. Element 56: wherein the catalyst is a hydrogen ferrierite form of zeolite. Element 57: wherein the catalyst is a zeolite catalyst having a silica-alumina ratio in the range of 1:5 to 1:100. Element 58: wherein the catalyst is a zeolite catalyst having a silica-alumina ratio in the range of 1:5 to 1:50. Element 59: wherein the catalyst is a zeolite catalyst having a silica-alumina ratio in the range of 1:10 to 1:20. Element 60: wherein the process further produces heavy compounds having 5 or more carbon atoms ("C5+ heavies"), and the production of C5+ heavies is reduced by at least 5% as compared to a process without steps (b) and (c). Element 61: wherein the process further produces heavy compounds having 5 or more carbon atoms ("C5+ heavies"), and the production of C5+ heavies is reduced by at least 10% as compared to a process without steps (b) and (c). Element 62: wherein the yield of the linear olefin is increased by at least 5% as compared to an isomerization process without steps (b) and (c). Element 63: wherein the yield of the linear olefin is increased by at least 10% as compared to an isomerization process without steps (b) and (c). Element 64: wherein the yield of the linear olefin is increased by at least 20% as compared to an isomerization process without steps (b) and (c). Element 65: wherein the catalyst may include a binder. Element 66: wherein the binder comprises silica, silica-alumina, bentonite, kaolin, bentonite with alumina, montmorillonite, attapulgite, titania and/or zirconia. Element 67: wherein the weight ratio of binder to zeolite is in the range from 1:10 to 10:1. Element 68: wherein the weight ratio of binder to zeolite is in the range of 1:10 to 5:1. Element 69: wherein the weight ratio of binder to zeolite is in the range of 1:5 to 10:1. Element 70: wherein the weight ratio of binder to zeolite is in the range of 1:5 to 5:1. Element 71: wherein the second temperature is at least 10° C. greater than the first temperature. Element 72: wherein the second temperature is at least 20° C. greater than the first temperature. Element 73: wherein the second temperature is at least 35° C. greater than the first temperature. Element 74: wherein the second temperature is at least 50° C. greater than the first temperature. Element 75: wherein the reactor is a packed bed reactor. Element 76: wherein the reactor is a fixed bed reactor. Element 77: wherein the reactor is a fluidized bed reactor. Element 78: wherein the reactor is a moving bed reactor. Element 79: wherein the catalyst bed of the moving bed reactor moves upwards. Element 80: additionally, comprising recovering iso-olefins from the reactor. Element 81: wherein the feed comprises at least 40 wt. % linear C4 olefin. Element 82: wherein the feed comprises at least 55 wt. % linear C4 olefin. Element 83: wherein the feed comprises at least 70 wt. % linear C4 olefin. Element 84: wherein the feed comprises at least 85 wt. % linear C4 olefin. Element 85: wherein the feed comprises at least 95 wt. % linear C4 olefin. Element 86: wherein the feed comprises at least 99 wt. % linear C4 olefin. Element 87: additionally, comprising recovering isobutylene from the reactor. Element 88: further comprising the step of recovering the at least one skeletal isomer from the reactor. Element 89: further comprising a second halting step and second resuming step. Element 90: wherein the at least one olefin is an iso-olefin. Element 91: wherein the at least one olefin is a linear olefin. Element 92: wherein the at least one olefin is isobutylene and the at least one skeletal isomer is 1-butene and 2-butene. Element 93: wherein the hydrocarbon feed comprises 1-butene and 2-butene, and said at least one skeletal isomer olefin is isobutylene. Element 94: wherein the hydrocarbon feed further comprises alkanes, aromatics, hydrogen and other gases. Element 95: wherein the first period of time is 1 to 3 hours long and the second period of time is 1 to 3 hours long. Element 96: wherein during the first period of time at least a portion of the olefin in the hydrocarbon feed is structurally isomerized to the at least one skeletal isomer. Element 97: wherein coking of the isomerization catalyst increases during the second period of time. Element 98: wherein the first temperature is within the range of about 380° C. to about 425° C. Element 99: wherein the second temperature is within the range of about 420° C. to about 450° C. Element 100: wherein the reactor is maintained at a pressure less than 345 kPa (50 psig) after resuming the hydrocarbon feed comprising the at least one olefin. Element 101: wherein the isomerization catalyst is a zeolite catalyst. Element 102: wherein the isomerization catalyst is a hydrogen ferrierite form of zeolite.

This summary is provided to introduce a selection of concepts that are further described below in the detailed description. This summary is not intended to identify key or essential features of the claimed subject matter, nor is it intended to be used as an aid in limiting the scope of the claimed subject matter.

DEFINITIONS

As used herein, the terms "skeletal isomerization" are used interchangeably to refer to an isomerization process that involves the movement of a carbon atom to a new location on the skeleton of the molecule, e.g., from a branched isobutylene skeleton to a linear or straight chain (not branched) butene skeleton. The product in the skeletal isomerization process is a skeletal isomer of the reactant. The term "skeletal isomer" refers to molecules that have the same number of atoms of each element and the same functional groups, but differ from each other in the connectivity of the carbon skeleton.

As used herein, the term "zeolite" includes a wide variety of both natural and synthetic positive ion-containing crystalline aluminosilicate materials, including molecular sieves. Zeolites are characterized as crystalline aluminosilicates which comprise networks of $SiO_4$ and $AlO_4$ tetrahedra in which silicon and aluminum atoms are cross-linked in a three-dimensional framework by sharing of oxygen atoms. This framework structure contains channels or interconnected voids that are occupied by cations, such as sodium, potassium, ammonium, hydrogen, magnesium, calcium, and water molecules. The water may be removed reversibly, such as by heating, which leaves a crystalline host structure available for catalytic activity. The term "zeolite" in this specification is not limited to crystalline aluminosilicates. The term as used herein also includes silicoaluminophosphates (SAPO), metal integrated aluminophosphates (MeAPO and ELAPO), metal integrated silicoaluminophosphates (MeAPSO and ELAPSO). The MeAPO, MeAPSO, ELAPO, and ELAPSO families have additional elements included in their framework. For example, Me represents the elements Co, Fe, Mg, Mn, or Zn, and El represents the elements Li, Be, Ga, Ge, As, or Ti. An alternative definition would be "zeolitic type molecular sieve" to encompass the materials useful for this disclosure.

As used herein, "crystal size" refers to the diameter of the zeolite crystals which exist in a zeolite catalyst; "channel size" refers to the size of the channels in the zeolite structure; and "pore size" refers to the size of the pore, or opening, in the zeolite structure.

As used herein, the term "coke" refers to the formation of carbonaceous materials on a catalyst surface, particularly inside and around the mouths of channels. As understood in the field, coke is the end product of carbon disproportionation, condensation and hydrogen abstraction reactions of adsorbed carbon-containing material.

As used herein, the term "unselective site" refers to an active site on the catalyst that catalyzes undesirable side reactions.

As used herein, "olefin" refers to any alkene compound that is made up of hydrogen and carbon that contains one or more pairs of carbon atoms linked by a double bond. A "C" followed by a number, in reference to an olefin, refers to how many carbon atoms the olefin contains. For example, a C4 olefin can refer to butene, butadiene, or isobutene. A plus sign (+) is used herein to denote a composition of hydrocarbons with the specified number of carbon atoms plus all heavier components. As an example, a C4+ stream comprises hydrocarbons with 4 carbon atoms plus hydrocarbons having 5 or more carbon atoms.

As used herein, WHSV or "weight hour space velocity" refers to the weight of feed flowing per hour per unit weight of the catalyst. For example, for every 1 gram of catalyst, if the weight of feed flowing is 100 gram per hour, then the WHSV is 100 hr$^{-1}$.

As used herein, "atmosphere" in the context of pressure refers to 101,325 Pascal, or 760 mmHg, or 14.696 psi.

The terms "heavy olefins" is used to denote compositions of C5+ hydrocarbons, including mono-olefins and diolefins.

The term "conversion" is used to denote the percentage of a component fed which disappears across a reactor.

The term "2-butene" as used herein refers to both cis-2-butene and trans-2-butene.

The term "linear C4 olefin" as used herein refers 1-butene, cis-2-butene and/or trans-2-butene.

The term "normal butene yield" refers to the amount of normal, linear butenes, including 1- and 2-butene, formed during the isomerization process.

As used herein, the term "raffinate" refers to a residual stream of olefins obtained after the desired chemicals/material have been removed. In the cracking/crude oil refining process, a butene or "C4" raffinate stream refers to the mixed 4-carbon olefin stream recovered from the cracker/fluid catalytic cracking unit. The term "Raffinate 1" refers to a C4 residual olefin stream obtained after separation of butadiene (BD) from the initial C4 raffinate stream. "Raffinate 2" refers to the C4 residual olefin stream obtained after separation of both BD and isobutylene from the initial C4 raffinate stream. "Raffinate 3" refers to the C4 residual olefin stream obtained after separation of BD, isobutylene, and 1-butene from the initial C4 raffinate stream. In some embodiments of the present disclosure, the isobutylene separated from Raffinate 1 can be used as a source for the skeletal isomerization process, especially when C4 alkanes have first been removed.

Use of the term "optionally" with respect to any element of a claim means that the element is required, or alternatively, not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, each range of values (of the form, "from about a to about b," or, equivalently, "from approximately a to b," or, equivalently, "from approximately a-b") disclosed herein is to be understood to set forth each number and range encompassed within the broader range of values.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The terms in the claims have their plain, ordinary meaning unless otherwise explicitly and unambiguously defined by the patentee. Moreover, the indefinite articles "a" or "an", as used in the claims, are defined herein to mean one or more than one of the elements that it introduces. If there is any conflict in the usages of a word or term in this specification and one or more patent or other documents, the definitions that are consistent with this specification should be adopted.

The following abbreviations are used herein:

| ABBREVIATION | TERM |
| --- | --- |
| B1 | 1-butene |
| B2 | 2-butene |
| EFF | effluent |
| FD | feed |
| H-FER | Hydrogen ferrierite |
| IB1 | Isobutylene |
| PO/TBA | propylene oxide/t-butyl alcohol |
| WHSV | Weight hour space velocity (mass feed rate per hour per mass of catalyst |
| wt. % | weight percent |

BRIEF DESCRIPTION OF THE DRAWINGS

FIG. 1B illustrates the conversion rate of isobutylene to linear C4 olefins, in accordance with embodiments of the disclosure.

FIG. 2B illustrates the conversion rate of isobutylene to linear C4 olefins for an embodiment of the disclosure with two different stagnation periods with no feed flow.

FIG. 4A illustrates the yield of isobutylene and C5+ heavies in accordance with embodiments of the disclosure using 1-butene as the hydrocarbon feed.

FIG. 4B illustrates the conversion rate of linear C4 olefins to isobutylene in accordance with embodiments of the disclosure using 1-butene as the hydrocarbon feed.

DETAILED DESCRIPTION

Figure 1A:
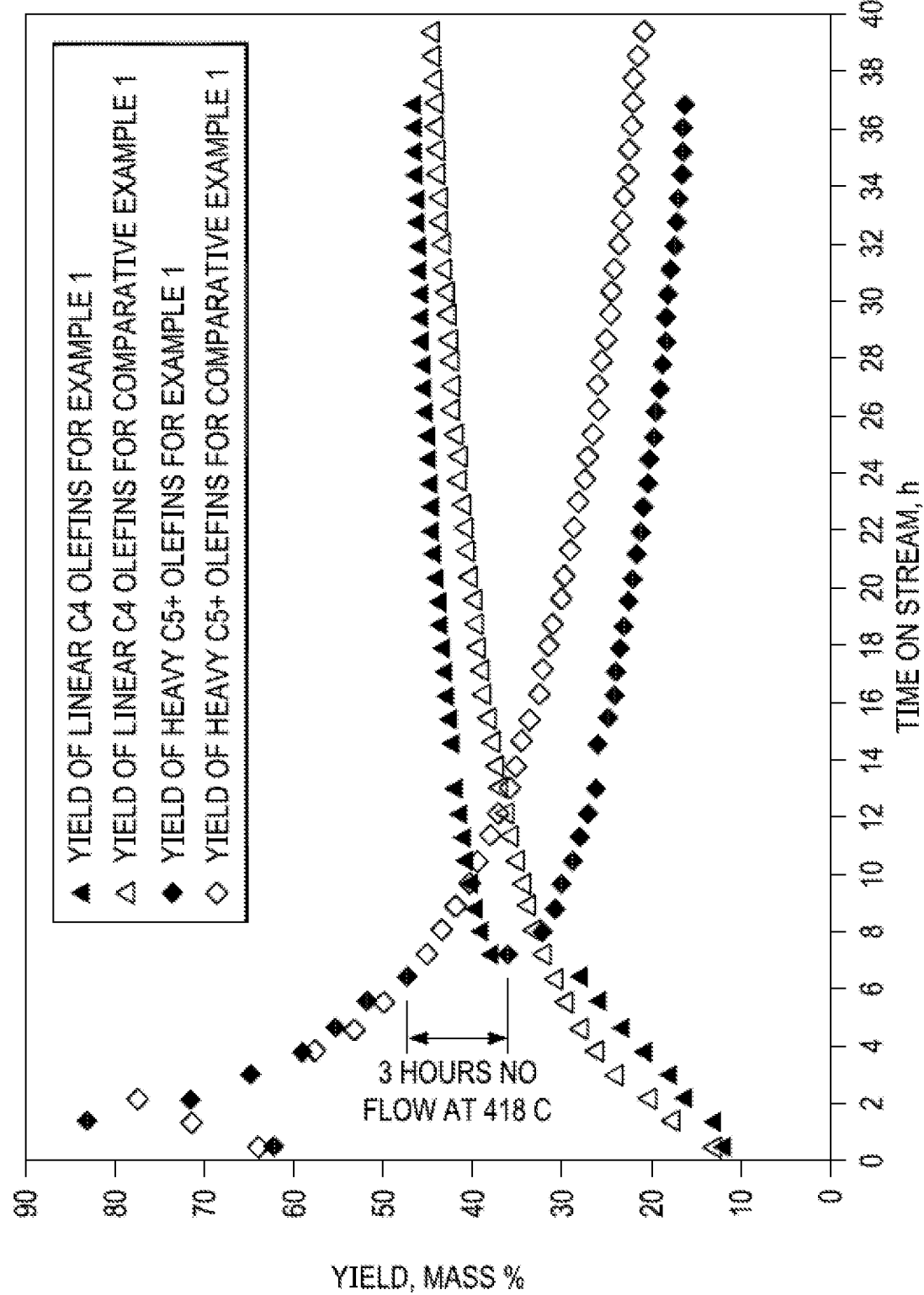
FIG. 1A illustrates the yield of linear C4 olefins and C5+ heavies, in accordance with embodiments of the disclosure.

The present disclosure provides improved methods of structurally isomerizing olefins, wherein the improvement comprises stopping the flow of feed for a period of time at least one time. This stoppage of flow allows for a stagnation period wherein a "beneficial" coking of the unselective sites on the catalyst occurs. This results in an increase in the yield of isomerization products. In some embodiments, when the feed contains C4 olefins, this method will also decrease the production of heavy olefins (C5+).

In more detail, the novel method comprises the steps of: (a) feeding a hydrocarbon feed that has at least one olefin into to a reactor having an isomerization catalyst at a hydrocarbon weight hour space velocity (WHSV) in the range of from 1 to 100 $hr^{-1}$ for a first period of time, wherein the reactor is maintained at a first temperature and a first pressure; (b) stopping the feeding for a second period of time, wherein the reactor is maintained at a second temperature; and (c) resuming the feeding of the hydrocarbon feed, wherein the reactor is maintained at a third temperature and a third pressure. The method can also include optional additional periods of time for stopping and resuming the feeding. The at least one olefin in the feed can have two to ten carbons. During each of the feeding steps (a) and (c), a portion of the at least one olefin is isomerized to at least one skeletal isomer olefin product. For example, if the at least one olefin is an iso-olefin such as isobutylene, then the skeletal isomer olefin product will be a linear olefin such as 1- or 2-butene. If the at least one olefin is a linear olefin such as 2-butene, then the skeletal isomer olefin product will be an iso-olefin such as isobutylene. The novel method can further comprise the step of recovering at least one skeletal isomer olefin product.

In some embodiments, the novel method comprises the steps of: (a) feeding a hydrocarbon feed that has at least one olefin into to a reactor having an isomerization catalyst at a hydrocarbon weight hour space velocity (WHSV) in the range of from 1 to 100 $hr^{-1}$ for a first period of time, wherein the reactor is maintained at a first temperature and a first pressure; (b) stopping the feeding for a second period of time, wherein the reactor is maintained at a second temperature; (c) resuming the feeding of the hydrocarbon feed, wherein the reactor is maintained at a third temperature and a third pressure; (d) stopping the feeding again for a fourth period of time, wherein the reactor is maintained at a fourth temperature; and (e) resuming the feeding of the hydrocarbon feed again, wherein the reactor is maintained at a fifth temperature and a fifth pressure. During each of the feeding steps (a), (c), and (e), a portion of the at least one olefin is isomerized to at least one skeletal isomer olefin product. The novel method can further comprise the step of recovering at least one skeletal isomer olefin product. In some methods, if the at least one olefin is an iso-olefin such as isobutylene, then the skeletal isomer olefin product will be a linear olefin such as 1- or 2-butene. If the at least one olefin is a linear olefin such as 2-butene, then the skeletal isomer olefin product will be an iso-olefin such as isobutylene.

In some embodiments of the novel method comprises the steps of: (a) feeding a hydrocarbon feed that has at least one iso-olefin into to a reactor having an isomerization catalyst at a hydrocarbon weight hour space velocity (WHSV) in the range of from 1 to 100 $hr^{-1}$ for a first period of time, wherein the reactor is maintained at a first temperature and a first pressure; (b) stopping the feeding for a second period of time, wherein the reactor is maintained at a second temperature; and (c) resuming the feeding of the hydrocarbon feed, wherein the reactor is maintained at a third temperature and a third pressure. The method can also include optional additional periods of time for stopping and resuming the feeding. During each of the feeding steps, a portion of the at least one iso-olefin is isomerized to at least one linear olefin, wherein the method further comprises the step of recovering the at least one linear olefin.

In other embodiments of the novel method comprises the steps of: (a) feeding a hydrocarbon feed that has at least one linear olefin into to a reactor having an isomerization catalyst at a hydrocarbon weight hour space velocity (WHSV) in the range of from 1 to 100 $hr^{-1}$ for a first period of time, wherein the reactor is maintained at a first temperature and a first pressure; (b) stopping the feeding for a second period of time, wherein the reactor is maintained at a second temperature; and (c) resuming the feeding of the hydrocarbon feed, wherein the reactor is maintained at a third temperature and a third pressure. The method can also include optional additional periods of time for stopping and resuming the feeding. During each of the feeding steps, a portion of the at least one linear is isomerized to at least one iso-olefin, wherein the method further comprises the step of recovering the at least iso-olefin.

More details on the skeletal isomerization process conditions and feeds are provided below.

Hydrocarbon Feedstream: The presently described methods are for the skeletal isomerization (both forward and reverse) of olefins, also known as alkenes. Thus, the hydrocarbon feedstream, or feed, used herein may comprises at least one olefin that will be isomerized into a skeletal isomer thereof. For example, an iso-olefin is a skeletal isomer of a linear olefin, and vice versa. In some embodiments, the at least one olefin in the hydrocarbon feed has two to ten carbon atoms.

In some embodiments, the hydrocarbon feed comprises unbranched linear, or normal, olefins having two to ten carbons, as well as other hydrocarbons such as alkanes, di-olefins, aromatics, hydrogen, and inert gases. In other embodiments, the feed comprises at least 40 wt. % of linear C4 olefins, as well as other hydrocarbons such as alkanes, other olefins, aromatics, hydrogen, and inert gases. Alternatively, the feed comprises at least 55 wt. % of linear C4 olefins, at least 70 wt. % of linear C4 olefins, at least 85 wt. % of linear C4 olefins, at least 95 wt. % of linear C4 olefins, or at least 99 wt. % of linear C4 olefins.

In other embodiments, the hydrocarbon feed used herein comprises branched olefins, also known as "iso-olefins". In this disclosure, the branched olefins can have four to ten carbon atoms. In some embodiments, the feed used herein comprises a methyl-branched iso-olefin. In some embodiments of the disclosure, the feed contains isobutylene. As before, the hydrocarbon feed used in some embodiments of the disclosure may also include other hydrocarbons such as alkanes, di-olefins, and aromatics, as well as hydrogen and other gases.

In some embodiments of the disclosure, the feed comprises at least 40 wt. % isobutylene, at least 55 wt. % isobutylene, at least 70 wt. % isobutylene, at least 85 wt. % isobutylene, at least 95 wt. % isobutylene, or at least 99 wt. % isobutylene. The isobutylene can be from any source. In some embodiments, the isobutylene comes from a Raffinate 1 stream derived from a cracker/fluid catalytic cracking unit and has had its C4 alkanes removed. Alternatively, the isobutylene can come from a stream derived from a propylene oxide/t-butyl alcohol (PO/TBA) plant. The dehydration of the t-butyl alcohol can result in a more purified isobutylene stream than a stream sourced from a cracker.

Isomerization Catalyst: The isomerization catalyst used in embodiments of this disclosure includes catalysts suitable to skeletally isomerize olefins. This includes isomerizing iso-olefins to linear, or normal, olefins (unbranched) and vice versa.

In some embodiments of the disclosure, the catalyst may comprise a zeolite and such catalysts may be referred to as a "zeolite catalyst". A zeolite catalyst used in embodiments of this disclosure may comprise a zeolite having one-dimensional channels with a channel diameter ranging from greater than about 0.42 nm to less than about 0.7 nm. Such zeolite catalysts may comprise zeolites channels with the specified diameter in one dimension. Zeolites having channel diameters greater than 0.7 nm are more susceptible to unwanted aromatization, oligomerization, alkylation, coking and by-product formation. However, under certain conditions, the coking may be beneficial, such as reducing the quantity of possible sites for the unwanted aromatization, oligomerization, alkylation.

Alternatively, the zeolite catalyst used in embodiments of this disclosure may comprise two or three-dimensional zeolites having a channel size greater than 0.34 nm in two or more dimensions permit dimerization and trimerization of the alkene. Hence, zeolites having a channel diameter bigger than about 0.7 nm in any dimension or having a two or three-dimensional channel structure in which any two of the dimensions has a channel size greater than about 0.42 nm, while not suitable for isomerization of isobutylene, may nevertheless be used in light of the preferential coking conditions described in the present disclosure. Examples of zeolites that can be used in the processes of this disclosure include the hydrogen form of ferrierite (H-FER), the hydrogen form of heulandite, the hydrogen form of stilbite, SAPO-11, SAPO-31, SAPO-41, ZSM-12, ZSM-22, ZSM-23, ZSM-35, and ZSM-48. The isotypic structures of these frameworks, known under other names, are considered to be equivalent.

In some embodiments of the present disclosure, the zeolite catalyst is H-ferrierite (H-FER). H-FER is derived from ferrierite, a naturally occurring zeolite mineral having a composition varying somewhat with the particular source. A typical elemental composition of ferrierite is described as:

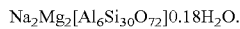

$Na_2Mg_2[Al_6Si_{30}O_{72}]0.18H_2O$.

The prominent structural features of ferrierite found by x-ray crystallography are perpendicular channels in the alumino-silicate framework—one with 8-membered rings in the [010] direction and one with 10-membered rings in the [001] direction. These channels, which are roughly elliptical in cross-section, are of two sizes: larger channels having major and minor axes of 0.54 and 0.42 nm, respectively, and smaller parallel channels having major and minor axes of 0.48 and 0.35 nm, respectively. Conversion of ferrierite to its hydrogen form, H-ferrierite, replaces sodium cations with hydrogen ions in the crystal structure, making it more acidic. Both the alkali metal and hydrogen forms reject multiple branched chain and cyclic hydrocarbon molecules and retard coke formation.

In some embodiments of the present disclosure, the H-FER catalyst has a $Na_2O$ content in the range of 0 to 0.10 wt. %. In some embodiments of the present disclosure, the H-FER catalyst has a $Na_2O$ content in the range of 0 to 0.05 wt. %. In some embodiments of the present disclosure, the H-FER catalyst has a $Na_2O$ content in the range of 0.05 to 0.10 wt. %. In some embodiments of the present disclosure, the H-FER catalyst has a $Na_2O$ content of 0 wt. %. In some embodiments of the present disclosure, the H-FER catalyst has a $Na_2O$ content less than 0.04 wt. %, a SAR of about 25, an XRD crystallinity of 96%, a BET surface area of 421 $m^2/g$, a crystal size (SEM) less than 200 nm, and a loss on ignition of about 9 wt. %. All relative amounts defined within this paragraph are based upon the total weight of the H-FER catalyst.

The zeolite catalyst used in embodiments of the present disclosure may be used alone or suitable combined with a refractory oxide that serves as a binder material. Suitable refractory oxides include, but are not limited to, natural clays, such as bentonite, montmorillonite, attapulgite, and kaolin; alumina; silica; silica-alumina; hydrated alumina; titania; zirconia and mixtures thereof. The weight ratio of binder material and zeolite suitably ranges from 1:10 to 10:1. In some embodiments of the disclosure, the weight ratio of binder to zeolite is in the range of 1:10 to 5:1, the range of 3:5 to 10:1, or the range of 3:5 to 8:5. In some embodiments of the present disclosure, the binder comprises from 10 wt. % to 20 wt. % of the catalyst-binder combination. In some embodiments of the present disclosure, the binder comprises from 10 wt. % to 15 wt. % of the catalyst-binder combination. In some embodiments of the present disclosure, the binder comprises from 15 wt. % to 20 wt. % of the catalyst-binder combination. In some embodiments of the present disclosure, the binder comprises from 13 wt. % to 17 wt. % of the catalyst-binder combination.

The catalyst in some embodiments of the presently disclosed methods, when combined with at least one binder, can be extruded into any shape. This includes, but is not limited to, spheres, pellets, tablets, platelets, cylinders, helical lobed extrudate, trilobes, quadralobes, multilobed (5 or more lobes), and combinations thereof.

In some embodiments, the catalyst is a pure zeolite powder. In other embodiments, the catalyst is a bound zeolite that has been extruded in a trilobed, quadralobe, or multilobed shape. In yet other embodiments, the catalyst is a pure H-FER powder. Alternatively, the catalyst is an H-FER that is bound and extruded in a trilobed, quadralobe, or multilobed shape.

Various ferrierite zeolites, including the hydrogen form of ferrierite, for some embodiments herein are described in U.S. Pat. Nos. 3,933,974, 4,000,248, 4,942,027, and 9,827,560, each incorporated by reference in their entirety herein. In some embodiments of the present disclosure, the zeolite catalyst may be a H-FER catalyst prepared in accordance with U.S. Pat. No. 9,827,560 B2. In other embodiments of the present disclosure, the zeolite catalyst is a commercially available catalyst including, but not limited to, ZD18018TL from Zeolyst International.

Operating Conditions for Skeletal Isomerization Process:
In embodiments of the disclosure, the hydrocarbon feed may be contacted with the isomerization catalyst under reaction conditions effective to skeletally isomerize the olefins therein. This contacting step may be conducted in the vapor phase by bringing a vaporized feed into contact with the solid isomerization catalyst. The hydrocarbon feed and/or catalyst can be preheated as desired.

The isomerization process of the disclosure may be carried out in a variety of reactor types. In some embodiments of the disclosure, the reactor is a packed bed reactor. In some embodiments of the disclosure, the reactor is a fixed bed reactor. In some embodiments of the disclosure, the reactor is a fluidized bed reactor. In some embodiments of the disclosure, the reactor is a moving bed reactor. In embodiments of the disclosure using a moving bed reactor, the catalyst bed may move upwards or downwards.

The isomerization conditions are split into at least three different periods of time. In the first period of time, the hydrocarbon feedsteam having at least one olefin is fed at one or more feed speeds, as measured by WHSV, into a reactor maintained at a first temperature for a first known period of time and allowed to contact the isomerization catalyst. In this first period, a portion of the at least one olefin reacts to form at least one skeletal isomer. In the second period of time, the hydrocarbon feed is halted for a second known period of time while the reactor is maintained at a second temperature. The interruption of the hydrocarbon feed will allow dimers or oligomers of the olefins to form in the channels of the catalyst and form coke in situ. In the third period of time, the hydrocarbon feed is once again fed at one or more feed speeds, as measured by WHSV, into the reactor maintained at a third temperature for a third known period of time and allowed to contact the isomerization catalyst. In the third period of time, the hydrocarbon feed has some isomerization products, and more skeletal isomers are formed, thus increasing the yield of the skeletal isomers compared to isomerization processes without the second and third periods of time. Additional periods of time for stopping and resuming hydrocarbon flow can be performed as well.

The isomerization conditions for each of the three periods of time are disclosed below.

I. First Period of Time

The isomerization conditions during the first period of time are as follows:

In some embodiments of the disclosure, the olefin-containing hydrocarbon feed is fed, at a first flow rate, into an isomerization catalyst-containing reactor for a first period of time, wherein the reactor has a first temperature and a first pressure.

The first temperature of the reactor is from about 250° C. to about 650° C. and the first pressure of the reactor is from about 0 to about 1034 kPa (150 psig). In some embodiments of the disclosure, the feed is introduced into the reactor at a first temperature of about 380° C. to about 425° C. and a first pressure from about 0 to about 345 kPa (50 psig).

The hydrocarbon feed flow rate in the first period of time has a WHSV that ranges from about 1 to 100 hr$^{-1}$, with or without a conventional diluent. Alternatively, the hydrocarbon feed flow rate has a WHSV that ranges from about 2 to about 50 hr$^{-1}$; alternatively, hydrocarbon feed flow rate has a WHSV that ranges from about 40 to 70 hr$^{-1}$; alternatively, hydrocarbon feed flow rate has a WHSV that ranges from about 60 to 100 hr$^{-1}$; alternatively, hydrocarbon feed flow rate has a WHSV that ranges from about 1 to 20 hr$^{-1}$; alternatively, hydrocarbon feed flow rate has a WHSV is 1, 1.5, 2, 2.5 hr$^{-1}$, or combinations thereof.

In embodiments, wherein the hydrocarbon feed comprises methyl branched iso-olefin, the WHSV feed rate ranges from about 10 to about 35 hr$^{-1}$.

The duration of the first period of time may depend on the type of olefin present in the hydrocarbon feed and the characteristics of the zeolite catalyst necessary to support isomerization. For example, for larger iso-olefin and smaller catalyst crystals, the first period of time may be shorter than for smaller iso-olefin and larger catalyst crystals. In some embodiments, the first period of time is long enough to allow the heavy C5+ olefin-prone sites on the catalyst to become occupied by these heavier hydrocarbons such that they can later be coked.

In some embodiments of the disclosure, the first period of time is between about 1 to about 6 hours, between about 2 to about 4 hours, or between about 3 to about 5 hours. Alternatively, the first period of time in some embodiments of the disclosure is about 2 hours, about 2.5 hours, about 3 hours, about 3.5 hours, or about 4 hours.

The first temperature may depend on the type of olefin and the characteristics of the catalyst necessary to support isomerization. In some embodiments of the disclosure, the first temperature is within the range of from about 300° C. to about 500° C.; alternatively, the first temperature is within the range of from about 350° C. to about 450° C.; alternatively, the first temperature is within the range of from about 375° C. to about 415° C.; alternatively, the first temperature is within the range of from about 400° C. to about 425° C.

During the first period of time, a portion of the olefins in the hydrocarbon feed are isomerized into at least one skeletal isomer.

II. Second Period of Time

At the end of the first period of time is the second period time. In the second period of time, the olefin-containing hydrocarbon feed is stopped for the duration of a second period of time to allow for preferential coking of the catalyst. Without being bound by theory, it is thought that during the stagnate second period, the channels in the zeolite are occupied by the at least one olefin in the hydrocarbon feed and possibly the dimerized or oligomerized molecules thereof. Without further olefin to drive those dimers and oligomers away from the channels, in situ coking is more likely to take place.

When the olefin-containing feed is stopped in favor of a preferential coking, the temperature is maintained at a second temperature for a second period of time. The second temperature may be the same as, less than, or higher than the first temperature. In some embodiments of the disclosure, the second temperature is higher than the first temperature. The elevated temperature, relative to the temperature of the first period, may contribute to a more extensive coking of the catalyst. In some embodiments of the disclosure, the second temperature is at least 10° C. greater than the first temperature, at least 20° C. greater than the first temperature, at least 35° C. greater than the first temperature, or at least 50° C. greater than the first temperature. In some embodiments of the disclosure, the second temperature is between about 350° C. to about 550° C.; alternatively, the second temperature is between about 420° C. to about 450° C.; alternatively, the second temperature is between about 420° C. to about 450° C. The pressure in the reactor is not changed, and remains the same as that in the first period of time.

The duration of the second period of time may vary depending on the type of olefin and catalyst used in the isomerization process. In some embodiments of the disclosure, the second period of time is the same as the first period of time. In some embodiments, the second period of time is longer than the first period of time. In some embodiments, the second period of time is shorter than the first period of time. In some embodiments of the disclosure, the second period of time is between 1 to 6 hours, between 2 to 4 hours, or between 3 to 5 hours. In some embodiments of the disclosure, the second period of time is 2 hours, 2.5 hours, 3 hours, 3.5 hours, or 4 hours.

III. Third Period of Time

At the end of the second period of time is the third period time. In the third period of time, the olefin-containing feed is fed for the duration of third period of time at a third temperature.

The third temperature may be the same as, less than, or higher than the first or second temperature. In some embodiments of the disclosure, the third temperature is lower than the second temperature. In some embodiments of the disclosure, the third temperature is at least 10° C. lower than the second temperature, at least 20° C. lower than the second temperature, at least 35° C. lower than the second temperature, or at least 50° C. lower than the second temperature. In yet other embodiments, the third temperature is the same as the first temperature. In some embodiments of the disclosure, the third temperature is between about 250° C. to about 650° C.; alternatively, the second temperature is between about 380° C. to about 425° C.; alternatively, the second temperature is between about 420° C. to about 450° C. The pressure in the reactor is not changed, and remains the same as that in the first and second period of time.

The duration of the third period of time may be the same as, greater, or lower than either the first or second period of time. In some embodiments of the disclosure, the third period of time is the same as the first period of time. In some embodiments, the third period of time is longer than the first period of time. In some embodiments, the third period of time is shorter than the first period of time. In some embodiments of the disclosure, the third period of time is between 1 to 6 hours, between 2 to 4 hours, or between 3 to 5 hours. In some embodiments of the disclosure, the third period of time is 2 hours, 2.5 hours, 3 hours, 3.5 hours, or 4 hours.

The hydrocarbon feed flow rate in the third period of time has a WHSV that is the same, greater than, or lower than the WHSV in the first period of time. In some embodiments, the WHSV ranges from about 1 to 100 $hr^{-1}$, with or without a conventional diluent. Alternatively, the hydrocarbon feed flow rate has a WHSV that ranges from about 2 to about 50 $hr^{-1}$; alternatively, hydrocarbon feed flow rate has a WHSV that ranges from about 40 to 70 $hr^{-1}$; alternatively, hydrocarbon feed flow rate has a WHSV that ranges from about 60 to 100 $hr^{-1}$; alternatively, hydrocarbon feed flow rate has a WHSV that ranges from about 1 to 20 $hr^{-1}$; alternatively, hydrocarbon feed flow rate has a WHSV is 1, 1.5, 2, 2.5 $hr^{-1}$, or combinations thereof.

In embodiments, the WHSV feed rates of a hydrocarbon feed having methyl branched iso-olefin ranges from about 10 to about 35 $hr^{-1}$.

During the third period of time, a portion of the olefins in the hydrocarbon feed are isomerized into at least one skeletal isomer. The at least one skeletal isomer can be recovered from the reactor during or after the third period of time.

IV. Optional Additional Stop/Start Periods

While only one flow stoppage period is needed to see positive increases in the formation of the skeletal isomers, additional stoppages may be desire after the third period of time. The operating conditions for these additional periods will be the same, or within the parameters described above for the second period of time (for a second stoppage) or the third period of time (for a second resumption of flow).

In some embodiments of the present methods, the periods with no feed flow can be separated by a period of at least one hour of feed flow. For example, a isomerization process may have, in sequential order, a first period of feed flow that lasts 1-3 hours, a second period that lasts 1-3 hours and has no feed flow, a third period that lasts 1-15 hours and has feed flow, a fourth period that lasts 1-3 hours and has no feed flow, and a fifth period that lasts 1-20 hours and has feed flow.

Each additional period of no fed flow is expected to increase the yield of the skeletal isomer products. However, the greatest increase in yield has been observed when the no feed flow period occurs within 1-5 hours of the start of the isomerization process. Regardless, even incremental improvements in the yield can mean the difference between a cost-effective isomerization process and one that is cost prohibited.

By performing a skeletal isomerization using the steps above, the yield of the skeletal isomer product increases compared to isomerization process that do not stop and resume flow in a second and third period of time. By halting the hydrocarbon feed in the second period of time and optionally increasing the temperature of the reactor in the second period of time to increasing coking, the yield of skeletal isomer product olefins obtained by embodiments of this disclosure is increased due to the longer life cycle and higher reaction rate. The yield of skeletal isomer product olefins obtained using embodiments of the disclosure may be at least 5% greater as compared to an isomerization process that does not include the preferential coking aspect of this disclosure. In some embodiments of the disclosure, the yield of skeletal isomer product olefins obtained may be at least 10% greater than a similar isomerization process that does not include the preferential coking aspect of this disclosure. In some embodiments of the disclosure, the yield of skeletal isomer product olefins obtained may be at least 15% greater than a similar isomerization process that does not include the preferential coking aspect of this disclosure.

Using the above described methods, the skeletal isomerization process is improved because a greater amount of structurally isomerized product, also called skeletal isomer olefin product, can be formed. In some embodiments, when the feed comprises C4 olefins, a greater amount of structurally isomerized product can be formed while forming less heavy C5+ olefins. This leads to a more cost-effective isomerization process for generating greater amounts of structurally isomerized C4 olefins.

EXAMPLES

The following examples are included to demonstrate embodiments of the appended claims using the above described system and methods of increasing the yield of structural isomerization products for an isobutylene feed. The example is intended to be illustrative, and not to unduly limit the scope of the appended claims. Those of skill in the art should appreciate that many changes can be made in the specific embodiments which are disclosed and still obtain a like or similar result without departing from the spirit and scope of the disclosure herein. In no way should the following examples be read to limit, or to define, the scope of the appended claims.

Hydrocarbon Feed. For Examples 1-3, the feed comprised 99.95 wt. % of isobutylene. The expected skeletal isomer product olefins for such as feed composition include 1-butene, trans-2-butene, and cis-2-butene.

For Example 4, the feed comprised 99.6 wt. % of 1-butene. The expected skeletal isomer product olefin for such as feed composition include isobutylene.

Calculations. For Examples 1-4 below, the conversion of reactants to products is calculated. Without being bound by theory, it is believed that during the isomerization reaction, equilibrium is achieved between, for example, the isobutylene, 1-butene and trans- and cis-2-butene. Therefore, for Examples 1-3 wherein isobutylene is the hydrocarbon feedstream, the calculation of conversion reflects the feed (FD) and effluent (EFF) concentrations of 1-butene (B1), 2-butene (B2), and isobutylene (IB1). Conversion is calculated as:

$$\% \text{ isobutylene Conversion} = \frac{(\text{wt } \% \text{ } IB1)FD - (\text{wt } \% \text{ } IB1)EFF}{(\text{wt } \% \text{ } IB1)FD} \times 100$$

Yield is calculated as $$\% \text{ linear butene Yield} = \frac{(\text{wt } \% \text{ } B1 + \text{wt } \% \text{ } B2)EFF - (\text{wt } \% \text{ } B1 + \text{wt } \% \text{ } B2)FD}{(\text{wt } \% \text{ } IB1)FD} \times 100$$

Development of equivalent equations for other olefin reactants and skeletal isomer products are well within the abilities of one with skill in the art. For instance, Example 4 utilizes 1-butene as the hydrocarbon feedsteam, the following equation is used for the determination of the conversion of linear C4 olefins to isobutylene:

$$\% \text{ linear } C4 \text{ butene Conversion} = 1 - \frac{(\text{wt } \% \text{ } B1)FD - (\text{wt } \% \text{ } B1 + \text{wt } \% \text{ } B2)EFF}{(\text{wt } \% \text{ } B1)FD} \times 100$$

Example 1: C4 Isomerization with Stop of Feed

Isomerization of isobutylene was performed in Example 1 using the method of this disclosure, and compared to Comparative Example 1 that does not have the stoppage in feed flow or resumption of flow step.

In accordance with the presently described methods, the method in Example 1 comprised running a feed comprising 99.95 wt. % of isobutylene through a fixed bed reactor at approximately 418° C. The fixed bed reactor contained a hydrogen ferrierite (H-FER) catalyst. No catalyst pretreatment was performed. The isobutylene feed was maintained at WHSV=2 for 1 hour, WHSV=1.5 for 1 hour, WHSV=1 for 1 hour, followed by a 3-hour period of no feed flow, before re-starting the isobutylene feed at WHSV=2 for the remainder of the process.

Comparative Example 1 was performed without the stoppage of feed flow and the subsequent re-starting of feed flow. The materials, reactors, and steps are the same as above, except that the WHSV of the isobutylene feed was maintained at 2 throughout Comparative Example 1 and there was no interruption of isobutylene feed.

The results for Example 1 and Comparative Example 1 are displayed in FIGS. 1A and 1B. FIG. 1A compares the yield, in mass percentage, of Example 1 with that of Comparative Example 1, with triangles representing linear C4 olefin yield and diamonds representing C5+ heavies yield. FIG. 1B compares isobutylene conversion, in percentage, of Example 1 with that of Comparative Example 1.

As shown in FIG. 1A, the yield of linear C4 olefins for Example 1 is lower than Comparative Example 1 during the first three hours (e.g. first time period) before the isobutylene feed was stopped in Example 1. At the end of the first three hours, the yield of linear C4 olefins for Example 1 was about 18% while that of Comparative Example 1 was about 24%. During the next three hours, the linear C4 olefin yield steadily increased for Comparative Example 1, rising to about 32% around hour 6. However, once the isobutylene feed was resumed at hour 6 for Example 1, the linear C4 olefin yield jumped from about 28% to about 38%. The linear C4 olefin yield of Example 1 remained higher than the linear C4 olefin yield for Comparative Example 1 throughout the remainder of the run.

It is worth noting that even after the interruption of isobutylene feed for 3 hours, the total yield of linear C4 olefin in Example 1 is still higher than Comparative Example 1, where isobutylene was continuously supplied to the reactor.

The yield of unwanted C5+ heavies was also reduced by temporarily halting the isobutylene feed in Example 1. As shown in FIG. 1A, both Example 1 and Comparative Example 1 show similar yield of C5+ through hour 6 (when the isobutylene feed was stopped from hour 3 to hour 6 in Example 1). After hour 6, the yield of C5+ in Example 1 drops from about 47% to about 35% (hour 6) and continues to decline. The C5+ heavies yield of Example 1 remained lower than that of Comparative Example 1 throughout the remainder of the experiments.

FIG. 1B compares isobutylene conversion of Example 1 and Comparative Example 1. As shown in FIG. 1B, the conversion of isobutylene drops in Example 1 from about 77% to about 67% due to the cessation of the feed. Considering the results of FIGS. 1A and 1B together, this 10% loss suggests that the reduction in isobutylene conversion is directly related to the reduction in C5+ yield.

Example 2: Two Flow Stoppages

Figure 2A:
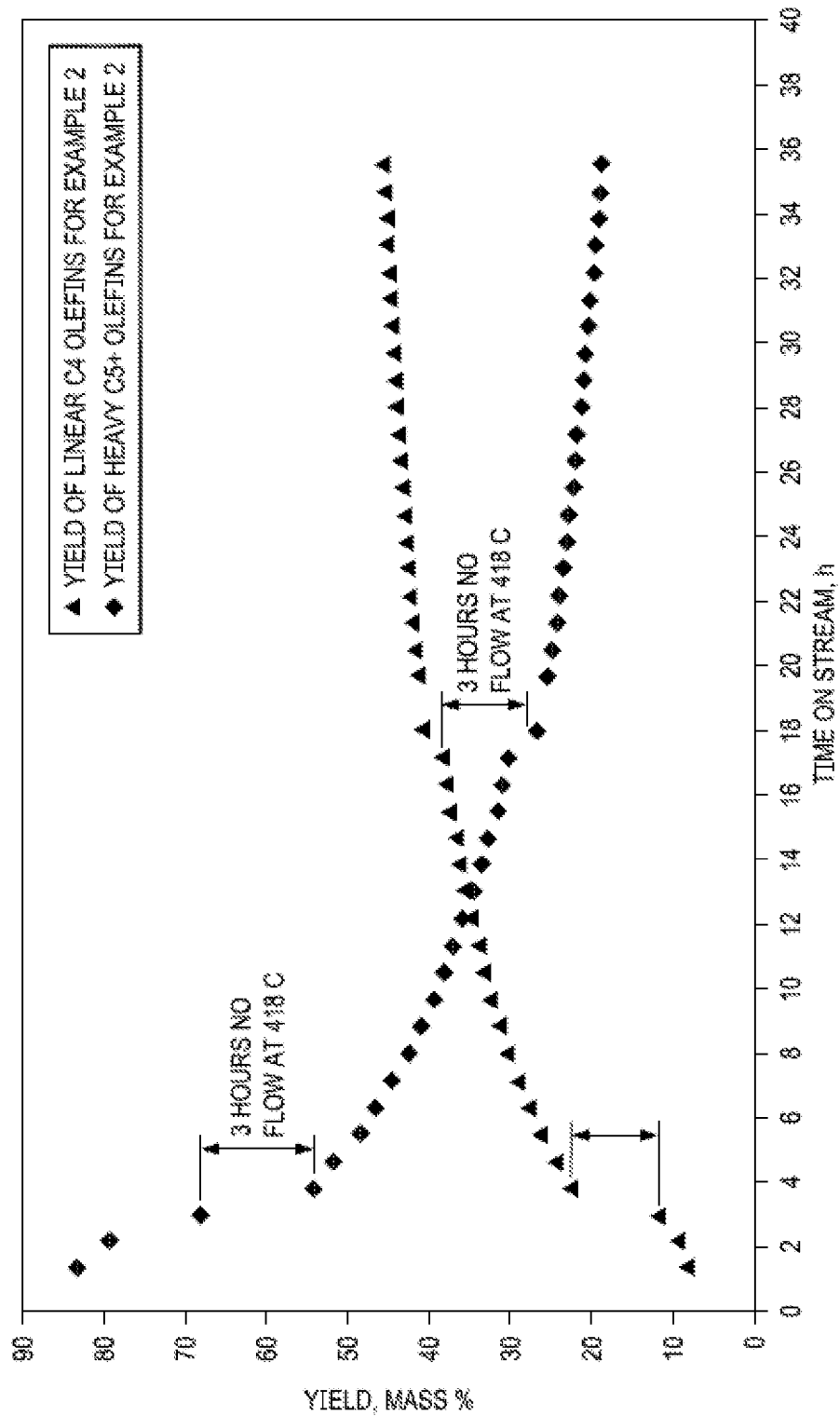
FIG. 2A illustrates the yield of linear C4 olefins and C5+ heavies for an embodiment of the disclosure with two different stagnation periods with no feed flow.

The effect of having more than one period of time without flow of the hydrocarbon feed into the reactor was evaluated. In Example 2, the same process setting as Example 1 was repeated, except there were two different 3-hour stoppages in flow. The first stoppage occurred at hour 3, like Example 1, and the second stoppage occurred at hour 17. The results are shown in FIGS. 2A-B.

The stagnation period performed at the beginning of the cycle in the first stoppage of flow was more effective in lowering isobutylene conversion, increasing linear C4 olefin yield, and suppressing heavy C5+ formation than the stagnation period performed 17 hours into the catalyst cycle. As shown in FIG. 2A, the amount of C5+ heavies dropped by about 10% in the first stoppage of flow, but only by about 3% in the second flow stoppage. In FIG. 2B, the first stoppage decreased the conversion of isobutylene by about 16% in the first stoppage of flow, and by about 3% in the second flow stoppage.

These results show that stop the flow early in the reaction process will result in improved production of desired isomerization products. However, two or more stagnation periods resulting from having no fed flow can be combined in a single isomerization process to further increase the yield of the skeletal isomer product olefin. As shown in Example 2, the use of two periods of no flow increased the yield of skeletal isomer products by a combined amount of 19%, while decrease the formation of heavy C5+ olefins by about 13%.

Example 3: Higher Temperature During Flow Stoppage

Figure 3A:
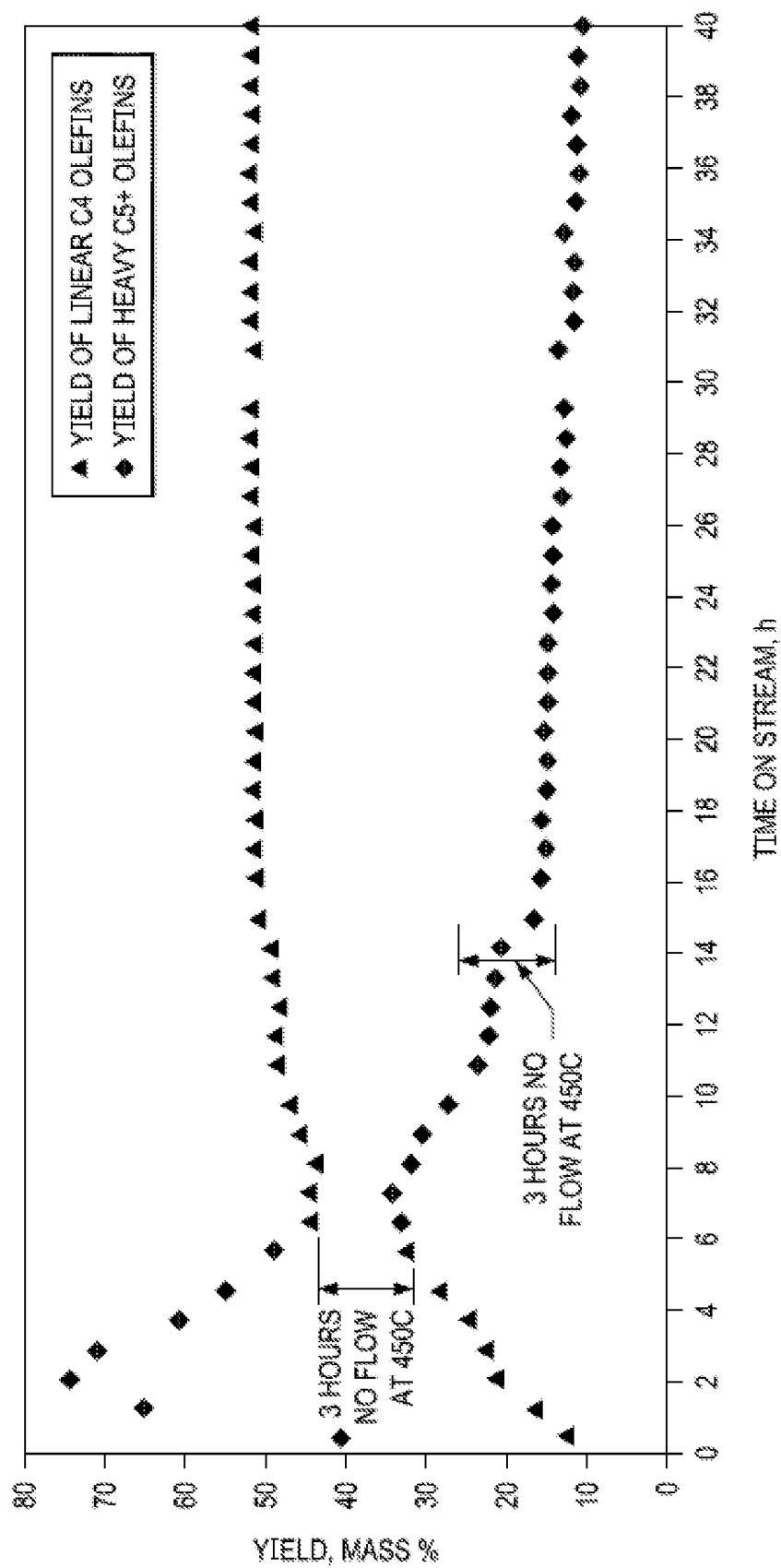
FIG. 3A illustrates the yield of linear C4 olefins and C5+ heavies for an embodiment of the disclosure with two different stagnation periods with no feed flow and higher reactor temperatures.
Figure 3B:
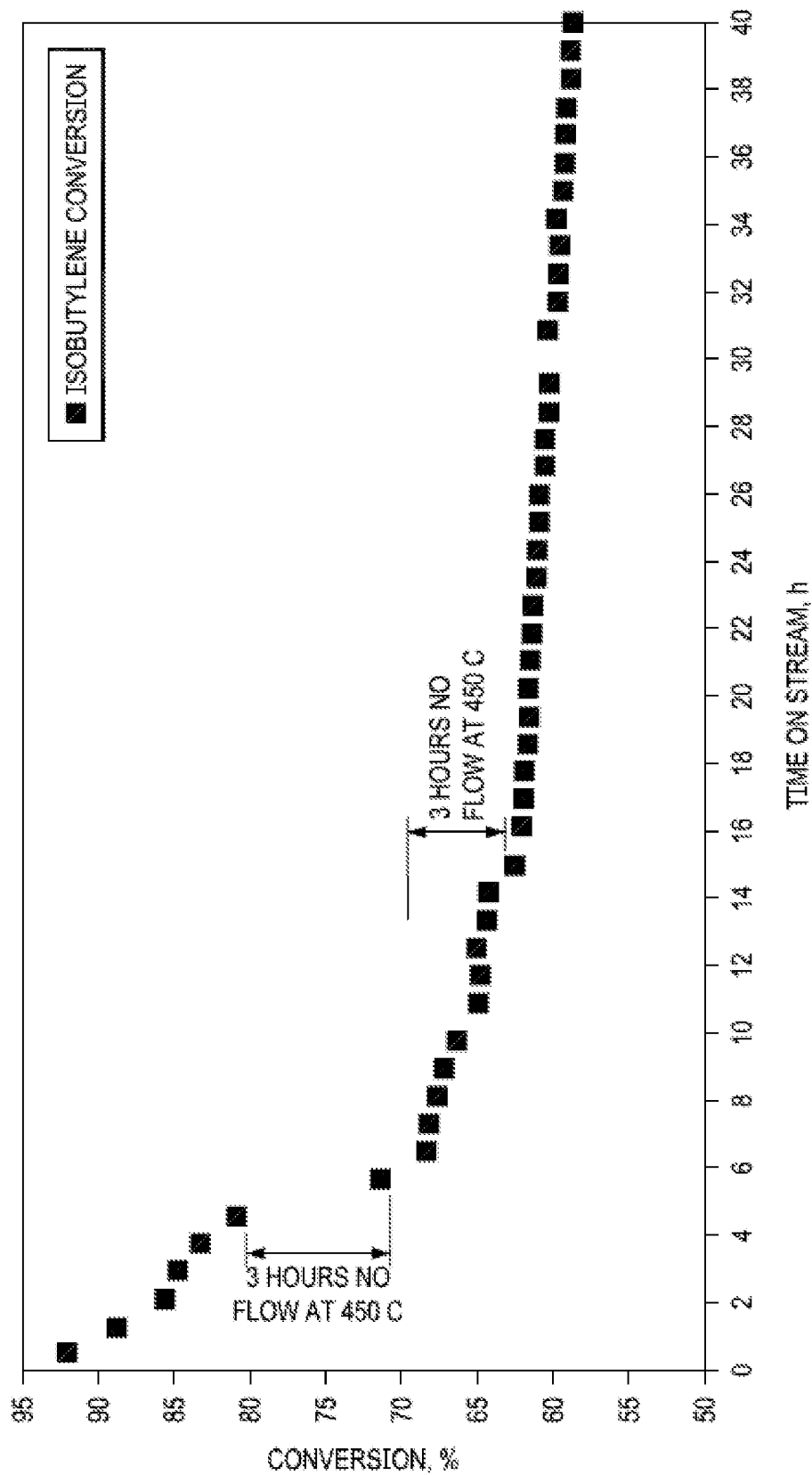
FIG. 3B illustrates the conversion rate of isobutylene to linear C4 olefins for an embodiment of the disclosure with two different stagnation periods with no feed flow and higher reactor temperatures.

The effect of having a stagnation period with a higher temperature than the reaction temperature was evaluated. In Example 3, the same process setting as Example 2 was repeated, except the reactor temperature during the 3-hour stagnation periods was increased from 418° C. to 450° C. at a rate of 10° C./min, held at 450° C., then returned to 418° C. before resuming the feed flow. The first stoppage occurred at hour 6 and the second stoppage occurred at hour 15. The results are shown in FIGS. 3A-B.

The stagnation period performed at the beginning of the cycle in the first stoppage of flow was more effective in increasing linear C4 olefin yield, and suppressing heavy C5+ formation than the soak performed 15 hours into the catalyst cycle. The suppression of the heavy C5+ lead to a decrease in the conversion of isobutylene. As shown in FIG. 3A, the amount of C5+ heavies dropped over 15% in the first stoppage of flow, but only by about 4% in the second flow stoppage. In FIG. 3B, the first stoppage decreased the conversion of isobutylene by about 20% in the first stoppage of flow, and by about 2% in the second flow stoppage.

These results show that increasing the reactor temperature during the stagnation period can further increase the yield of the skeletal isomer product olefin. The yield of linear C4 olefin is maximized much earlier in the cycle with the flow stoppage.

Example 4: Reversing Isomerization Direction with Feed Stoppages

Although Examples 1-3 are described in terms of isomerizing an iso-olefin to linear olefin, embodiments of the disclosure are applicable to the isomerization of a linear olefin to an iso-olefin.

Isomerization of 1-butene was performed in this example, using the method of this disclosure, and compared to Comparative Example 4 that does not have the stoppage in feed flow or resumption of flow step.

In accordance with the presently described methods, the method in Example 4 comprised running a feed comprising 99.6 wt. % of 1-butene through a fixed bed reactor at approximately 418° C. The fixed bed reactor contained the same hydrogen ferrierite (H-FER) catalyst of Example 1. No catalyst pretreatment was performed. The 1-butene feed was maintained at WHSV=2 for 6 hours, followed by a 3-hour period of no feed flow at the same temperature (418° C.), before re-starting the 1-butene feed at WHSV=2 for the remainder of the process.

Comparative Example 4 was performed without any stoppage of feed flow. The materials, reactors, and steps are the same as above, except that the WHSV of the 1-butene feed was maintained at WHSV=2 throughout Comparative Example 4 and there was no interruption of 1-butene feed flow.

The results for Example 4 and Comparative Example 4 are displayed in FIGS. 4A and 4B respectively. FIG. 4A compares the yield, in mass percentage, of Example 4 with that of Comparative Example 4, with triangles representing isobutylene yield and diamonds representing C5+ heavies yield. FIG. 4B compares linear C4 olefin conversion (both 1-butene in feed and 2-butene produced during the reaction), in percentage, of Example 4 with that of Comparative Example 4.

As shown in FIG. 4A, the yield of isobutylene for Example 4 is about the same as Comparative Example 4 during the first six hours before the 1-butene feed was stopped in Example 4. However, once the 1-butene feed was resumed at hour 6 for Example 4, the isobutylene yields increased from about 22% to about 32%. The isobutylene yield of Example 4 remained higher than the isobutylene yield for Comparative Example 4 until about 40 hours run time where they become similar.

The yield of unwanted C5+ heavies was also reduced. As shown in FIG. 4A, both Example 4 and Comparative Example 4 show similar yield of C5+ heavies through hour 6 (when the 1-butene feed was stopped in Example 4). After hour 6, the yield of C5+ heavies in Example 4 drops from about 48% to about 32% (hour 6) and continues to decline. The C5+ heavies yield of Example 4 remained lower than that of Comparative Example 4 throughout the remainder of the experiments.

FIG. 4B compares the linear C4 olefin conversion of Example 4 and Comparative Example 4. As shown in FIG. 4B, the conversion of linear C4 olefins drops in Example 4 from about 68% to about 53% after the cessation of the feed. Considering the results of FIGS. 4A and 4B together, this 15% difference in conversion of linear C4 olefin suggests that the reduction is directly related to the reduction in C5+ heavies yield.

The particular embodiments disclosed above are merely illustrative, as the present disclosure may be modified and practiced in different but equivalent manners apparent to those skilled in the art having the benefit of the teachings herein. Furthermore, no limitations are intended as to the details of construction or design herein shown, other than as described in the claims below. It is therefore evident that the particular illustrative embodiments disclosed above may be altered of modified and such variations are considered within the scope and spirit of the present disclosure. Alternative embodiments that result from combining, integrating, and/or omitting features of the embodiment(s) are also within the scope of the disclosure.

The following references are incorporated by reference in their entirety for all purposes.

U.S. Pat. No. 5,648,585
U.S. Pat. No. 6,111,160
U.S. Pat. No. 6,323,384
Atlas of Zeolite Structure Types" by W. M. Meier and D. H. Olson, Butterworths, 2nd Edition, 1987.
Collett and McGregor, Things go better with coke: the beneficial role of carbonaceous deposits in heterogeneous catalysis, *Catal. Sci. Technol.,* 2016, 6, 363-378.
Guisnet et al., Skeletal Isomerization of n-Butenes, *J. of Catalysis* 158, 551-560 (1996).

The invention claimed is:

1. A skeletal isomerization process comprising the steps of:
    (a) feeding a hydrocarbon feed comprising at least one olefin, for a first period of time in a range from 1 to 3 hours, at a weight hourly space velocity (WHSV) in a range of from 1 to 100 $hr^{-1}$ to a reactor containing an isomerization catalyst comprising a zeolite catalyst, wherein the reactor is maintained at a first temperature in a range of from about 380° C. to about 425° C. during the first period of time;
    (b) halting the feeding of the hydrocarbon feed comprising at least one olefin to the reactor for a second period of time in a range of 1 to 3 hours, wherein the reactor is maintained at a second temperature in a range of from about 420° C. to about 450° C. during the second period of time, wherein coking of the isomerization catalyst increases during the second period of time; and (c) resuming the feeding of the hydrocarbon feed comprising at least one olefin to the reactor for a third period of time, wherein at least a portion of the at least one olefin in the hydrocarbon feed is isomerized to at least one skeletal isomer and wherein the reactor is maintained at a third temperature during the third period of time.

2. The skeletal isomerization process of claim 1, further comprising the step of recovering the at least one skeletal isomer from the reactor.

3. The skeletal isomerization process of claim 1, wherein the process further produces heavy compounds having 5 or more carbon atoms ("C5+ heavies") and the production of C5+ heavies is reduced by at least 5% as compared to a process without steps (b) and (c).

4. The skeletal isomerization process of claim 1, wherein the yield of the at least one skeletal isomer is increased by at least 5% as compared to a process without steps (b) and (c).

5. The skeletal isomerization process of claim 1, further comprising a second halting and second resuming step.

6. The skeletal isomerization process of claim 1, wherein the at least one olefin is an iso-olefin.

7. The skeletal isomerization process of claim 1, wherein the at least one olefin is a linear olefin.

8. The skeletal isomerization process of claim 1, wherein the at least one olefin is isobutylene and the at least one skeletal isomer is 1-butene and 2-butene.

9. The skeletal isomerization process of claim 1, wherein the hydrocarbon feed comprises 1-butene and 2-butene, and the at least one skeletal isomer olefin is isobutylene.

10. The skeletal isomerization process of claim 1, wherein the hydrocarbon feed further comprises alkanes, aromatics, hydrogen and other gases.

11. The skeletal isomerization process of claim 1, wherein the hydrocarbon feed comprises at least 40 wt. % isobutylene.

12. The skeletal isomerization process of claim 1, wherein during the first period of time at least a portion of the olefin in the hydrocarbon feed is structurally isomerized to the at least one skeletal isomer.

13. The skeletal isomerization process of claim 1, wherein the third temperature is the same as the first temperature or different than the first temperature.

14. The skeletal isomerization process of claim 1, wherein the reactor is maintained at a pressure less than 345 kPa (50 psig) after resuming the hydrocarbon feed comprising the at least one olefin.

15. The skeletal isomerization process of claim 1, wherein the isomerization catalyst is a hydrogen ferrierite form of zeolite.

* * * * *